US009775932B2

(12) United States Patent
Desai et al.

(10) Patent No.: US 9,775,932 B2
(45) Date of Patent: Oct. 3, 2017

(54) NANOSTRUCTURE SURFACE COATED MEDICAL IMPLANTS AND METHODS OF USING THE SAME

(75) Inventors: Tejal A. Desai, San Francisco, CA (US); Ketal C. Popat, Fort Collins, CO (US); Craig A. Grimes, Boalsburg, PA (US)

(73) Assignees: The Regents of the University of California, Oakland, CA (US); The Penn State Research Foundation, University Park, PA (US)

( * ) Notice: Subject to any disclaimer, the term of this patent is extended or adjusted under 35 U.S.C. 154(b) by 1114 days.

(21) Appl. No.: 12/530,015

(22) PCT Filed: Mar. 17, 2008

(86) PCT No.: PCT/US2008/057261
§ 371 (c)(1),
(2), (4) Date: Mar. 1, 2011

(87) PCT Pub. No.: WO2008/115883
PCT Pub. Date: Sep. 25, 2008

(65) Prior Publication Data
US 2012/0114734 A1 May 10, 2012

Related U.S. Application Data

(60) Provisional application No. 60/895,306, filed on Mar. 16, 2007, provisional application No. 60/911,424, filed on Apr. 12, 2007.

(51) Int. Cl.
A61K 38/18 (2006.01)
A61L 27/54 (2006.01)
(Continued)

(52) U.S. Cl.
CPC ............ *A61L 27/54* (2013.01); *A61C 8/0012* (2013.01); *A61F 2/0077* (2013.01);
(Continued)

(58) Field of Classification Search
CPC ............................... D04H 13/00; A61K 38/18
(Continued)

(56) References Cited

U.S. PATENT DOCUMENTS 6,030,829 A 2/2000 Dannoux et al.
2004/0076681 A1* 4/2004 Dennis ................ A61K 9/0092
424/489

(Continued)

OTHER PUBLICATIONS

Bauer et al. "An indirect comparison of third-body wear in retrieved hydroxyapatite-coated, porous, and cemented femoral components" Clin Orthop Relat Res ,1994, 298:11-18.
(Continued)

*Primary Examiner* — Yashita Sharma
(74) *Attorney, Agent, or Firm* — Edward J. Baba; Khin K. Chin; Bozicevic, Field & Francis LLP

(57) ABSTRACT

Compositions including a surface or film comprising nanofibers, nanotubes or microwells comprising a bioactive agent for elution to the surrounding tissue upon placement of the composition in a subject are disclosed The compositions are useful in medical implants and methods of treating a patient in need of an implant, including orthopedic implants, dental implants, cardiovascular implants, neurological implants, neurovascular implants, gastrointestinal implants, muscular implants, and ocular implants.

23 Claims, 9 Drawing Sheets

(51) Int. Cl.
  *A61C 8/00* (2006.01)
  *A61F 2/00* (2006.01)
  *A61F 2/30* (2006.01)

(52) U.S. Cl.
  CPC . *A61F 2/30767* (2013.01); *A61F 2002/30064* (2013.01); *A61F 2002/3084* (2013.01); *A61F 2310/0061* (2013.01); *A61F 2310/0097* (2013.01); *A61F 2310/00401* (2013.01); *A61F 2310/00407* (2013.01); *A61F 2310/00413* (2013.01); *A61F 2310/00437* (2013.01); *A61F 2310/00461* (2013.01); *A61F 2310/00544* (2013.01); *A61F 2310/00598* (2013.01); *A61F 2310/00604* (2013.01); *A61F 2310/00616* (2013.01); *A61F 2310/00634* (2013.01); *A61F 2310/00976* (2013.01); *A61F 2310/00988* (2013.01); *A61L 2300/222* (2013.01); *A61L 2300/252* (2013.01); *A61L 2300/256* (2013.01); *A61L 2300/258* (2013.01); *A61L 2300/404* (2013.01); *A61L 2300/406* (2013.01); *A61L 2300/41* (2013.01); *A61L 2300/414* (2013.01); *A61L 2300/416* (2013.01); *A61L 2300/602* (2013.01); *A61L 2400/12* (2013.01)

(58) Field of Classification Search
  USPC ......... 623/13.11, 13.17, 20.17, 23.57–23.63, 623/23.72–23.76; 424/427; 977/778–783, 795, 809; 428/292.1
  See application file for complete search history.

(56) References Cited

U.S. PATENT DOCUMENTS

2004/0258726 A1   12/2004  Stupp
2005/0221072 A1*  10/2005  Dubrow et al. ........... 428/292.1
2006/0093642 A1    5/2006  Ranade
2006/0204738 A1    9/2006  Dubrow
2006/0229715 A1   10/2006  Istephanous et al.

OTHER PUBLICATIONS

Bloebaum et al. "Complications with hydroxyapatite particulate separation in total hip arthroplasty" Clin Orthop Relat Res, 1994, 298:19-26.

Bobyn et al. "The optimum pore size for the fixation of porous-surfaced metal implants by the ingrowth of bone" Clin Orthop Relat Res 1980, 150:263-70.

Tiedeman et al. "The role of a composite, demineralized bone matrix and bone marrow in the treatment of osseous defects" Orthopedics, 1995, 18(12):1153-1158.

Emerich and Thanos, "The pinpoint promise of nanoparticle-based drug delivery and molecular diagnosis," Biomolecular Engineering, vol. 23, No. 4, pp. 171-184 (2006).

\* cited by examiner

A.

B.

NANOSTRUCTURE SURFACE COATED MEDICAL IMPLANTS AND METHODS OF USING THE SAME

CROSS-REFERENCE

This application claims the benefit of U.S. Provisional Application No. 60/895,306 filed Mar. 16, 2007, and U.S. Provisional Application No. 60/911,424, filed on Apr. 12, 2007, which applications are incorporated herein by reference in their entirety.

BACKGROUND OF THE INVENTION

Total joint replacement is an effective treatment for relieving pain and restoring function for patients with damaged or degenerative joints. Approximately 500,000 total hip and knee replacements are performed each year in the United States. Although many of the outcomes are successful, there are still significant problems with implant loosening and failure. In fact, 25% of hip replacement surgeries were revisions due to previous implant failure. Surgery to replace these failures is more difficult and costly to perform and has a poorer outcome than the original joint replacement surgery. If fixation is not sufficient, loosening and osteolysis of the implant can occur. To overcome this problem, it is thought that bone implant materials need to stimulate rapid bone regeneration in order to fill in deficient bone and fix the implant firmly with the adjacent bone. The material surface must be able to recruit bone forming cells, such as osteoblasts, such that they can colonize and synthesize new bone tissue.

In order to design better implant materials, it is important to understand the events at the bone-material interface. As mentioned earlier, one of the important challenges is to induce bone growth on the implant surface. The level of bone growth depends on the surface characteristics of the implant. The first event that occurs after the implantation of a biomaterial is the adsorption of proteins from blood and other tissue fluids. Primarily, a hematoma, swelling filled with blood due to a break in the blood vessel, is present between the implant and bone. Cytokines and growth factors stimulate the recruitment of mesenchymal cells which differentiate into osteoblast that are responsible for bone formation. Over time, woven bone matures into lamellar bone which further strengthens the bone-implant interface. Thus, the surface properties play a critical role in long term stability and functionality of the implant.

In an attempt to enhance the stability of endosseous implants, a large number of implant materials and designs have been used. In addition to cement-based prosthetics, much attention in recent years has turned to microinterlocked implants, which have microporous surfaces to allow for the ingrowth of bone. Early work using oxide ceramics showed that a minimum interconnected pore diameter of approximately 100 µm was needed for adequate bone ingrowth (Hulbert et al., J Biomed Mater Res 1972; 6(5): 347-74). It was thought that smaller pore sizes allowed incomplete mineralization of the infiltrating tissue. Subsequent use of metallic implants showed bone ingrowth with pore sizes between 50 and 400 µm (Bobyn et al., Clin Orthop Relat. Res 1980(150):263-70). However, recent studies have revealed the possibility that much smaller pores may allow bone ingrowth when presented at high density within metal-oxide substrates. For example, nanoporous Ca—P coatings on implants have shown apposition of human bone growth within 2-3 weeks post surgery (Lee et al., J Biomed Mater Res 2001; 55(3):360-7). Osteoblasts cultured on ceramics of different nm-scale textures also exhibit altered morphologies and growth rates (Boyan et al., Biomaterials 1996, 17(2): 137-46; Popat et al., J Orthop Res 2006, 24(4):619-27; Popat et al., Biomaterials 2005, 26(22):4516-22; Swan et al., Biomaterials 2005, 26(14):1969-76; Swan et al., J Biomed Mater Res A 2005, 72(3):288-95; Webster et al., Biomaterials 2004, 25(19):4731-9; Webster et al., J Biomed Mater Res A 2003, 67(3):975-80; Webster et al., Biomaterials 2000, 21(17):1803-10). Nonetheless, there are several problems related to dissolution of nanoscale coatings over time, and cracking and separation from the metallic substrate (Bauer et al., Clin Orthop Relat Res 1994, (298):11-8; and Bloebaum et al., Clin Orthop Relat Res 1994, (298):19-26). These studies point to the importance of developing more robust and flexible nanoscale architectures to enhance the apposition of bone from existing bone surfaces and stimulate new bone formation.

This invention described below addresses these needs, as well as others.

SUMMARY OF THE INVENTION

The present invention provides compositions including a surface or film comprising nanofibers, nanotubes, or microwells, comprising a bioactive agent for elution to the surrounding tissue upon placement in a subject. The compositions are useful as medical implants, including orthopedic implants, dental implants, cardiovascular implants, neurological implants, neurovascular implants, gastrointestinal implants, muscular implants, and ocular implants. The present invention also provides methods of treating a patient in need of such an implant.

The present invention provides a medical implant including a surface or film comprising a plurality of nanofibers, nanotubes, or microwells, where said nanofibers, nanotubes, or microwells comprise a bioactive agent for elution to the surrounding tissue upon placement in a subject. In some embodiments, the medical implant is an orthopedic implant, a dental implant, a cardiovascular implant, a neurological implant, a neurovascular implant, a gastrointestinal implant, a muscular implant, or an ocular implant. In some embodiments, the medical implant is a patch for localized delivery of said bioactive agent to a soft tissue. In some embodiments, the surface or film expands or unfurls in the presence of a hydrating liquid. In some embodiments, the surface or film further includes cells, such as a stem cell, a retinal progenitor cell, a cardiac progenitor cell, an osteoprogenitor cell, or a neuronal progenitor cell.

In some embodiments, the at least one of said plurality of nanofibers, nanotubes, or microwells further comprises an erodible capping film to provide for delayed elution of said bioactive agent. In some embodiments, the surface or film comprises a plurality of at least two of nanofibers, nanotubes, and microwells, wherein one of said nanofibers, nanotubes, and microwells further comprises an erodible capping film to provide for delayed elution of said bioactive agent.

In some embodiments, the surface or film is comprised of poly(DL-lactide-co-glycolide) (PLGA), poly(DL-lactide-co-ε-caprolactone) (DLPLCL), poly(ε-caprolactone) (PCL), collogen, gelatin, agarose, poly(methyl methacrylate), galatin/ε-caprolactone, collagen-GAG, collagen, fibrin, PLA, PGA, PLA-PGA co-polymers, poly(anhydrides), poly(hydroxy acids), poly(ortho esters), poly(propylfumerates), poly(caprolactones), poly(hydroxyvalerate), polyamides, polyamino acids, polyacetals, biodegradable polycyanoacrylates, biodegradable polyurethanes and polysaccharides, polypyrrole, polyanilines, polythiophene, polystyrene, polyesters, non-biodegradable polyurethanes, polyureas, poly(ethylene vinyl acetate), polypropylene, polymethacrylate, polyethylene, polycarbonates, poly(ethylene oxide), co-polymers of the above, mixtures of the above, and adducts of the above, or combinations thereof.

In some embodiments, the surface or film is comprised of silicon, titania, zirconia, cobalt-chromium, alumina, silica, barium aluminate, barium titanate, iron oxide, and zinc oxide, nitinol, elastinite, tantalum, elgiloy, phynox, Ti6Al4V, CoCr, TiC, TiN, L605, 316, MP35N, MP20N, stainless steel alloy, 316L stainless steel alloy, 304 stainless steel alloy, or combinations thereof.

In some embodiments, the surface or film further includes a covalently attached bioactive agent. In some embodiments, the nanofibers, nanotubes, or microwells further include an agent to facilitate cell adhesion and cell growth selected from the group consisting of laminin, fibrin, fibronectin, proteoglycans, glycoproteins, glycosaminoglycans, chemotactic agents, and growth factors. In some embodiments, the bioactive agent is selected from a polypeptide, growth factor, a steroid agent, an antibody therapy, an antibody fragment, a DNA, an RNA, and siRNA, an antimicrobial agent, an antibiotic, an antiretroviral drug, an anti-inflammatory compound, an antitumor agent, anti-angiogeneic agent, and a chemotherapeutic agent.

In some embodiments, the nanofibers or nanotubes range in length from about 1 µm to about 500 µm, such as from about 1 µm to about 70 µm. In some embodiments, the nanofibers or nanotubes range in diameter from about 3 nm to about 300 nm. In some embodiments, the nanotubes have a pore diameter range from about 3 nm to about 250 nm. In some embodiments, the surface or film comprises nanofibers at a density greater than 100,000,000 nanofibers per square centimeter. In some embodiments, the surface or film comprises nanotubes at a density greater than 10,000,000 nanotubes per square centimeter. In some embodiments, the surface or film comprises nanofibers at a density greater than 25,000,000 nanofibers per square centimeter, wherein said density provides for an extracellular matrix compatible tissue adhesive. In some embodiments, the surface or film comprises nanotubes at a density greater than 25,000,000 nanotubes per square centimeter, wherein said density provides for an extracellular matrix compatible tissue adhesive.

In some embodiments, the said surface or film ranges in thickness from about 1 µm to about 2.5 mm, such as from about 1 µm to about 750 µm, including from about 1 µm to about 200 µm, and from about 1 µm to about 150 µm.

In some embodiments, the microwells range in diameter from about 1 µm to about 150 µm. In some embodiments, the microwells range in diameter from about 1 µm to about 150 µm. In some embodiments, the surface or film comprises microwells at a density greater than 150,000 microwells per square centimeter.

The present invention also provides a method of treating a patient in need of a medical implant, by placing a medical implant into the patient, wherein the medical implant comprises a surface or film comprising a plurality of nanofibers, nanotubes, or microwells, where said nanofibers, nanotubes, or microwells comprise a bioactive agent for elution to the surrounding tissue upon placement in a subject. In some embodiments, the medical implant is an orthopedic implant, a dental implant, a cardiovascular implant, a neurological implant, a neurovascular implant, a gastrointestinal implant, a muscular implant, or an ocular implant. In some embodiments, the medical implant is a patch for localized delivery of said bioactive agent to a soft tissue. In some embodiments, the surface or film expands or unfurls in the presence of a hydrating liquid. In some embodiments, the surface or film further includes cells, such as a stem cell, a retinal progenitor cell, a cardiac progenitor cell, an osteoprogenitor cell, or a neuronal progenitor cell.

In some embodiments, the at least one of said plurality of nanofibers, nanotubes, or microwells further comprises an erodible capping film to provide for delayed elution of said bioactive agent. In some embodiments, the surface or film comprises a plurality of at least two of nanofibers, nanotubes, and microwells, wherein one of said nanofibers, nanotubes, and microwells further comprises an erodible capping film to provide for delayed elution of said bioactive agent.

In some embodiments, the surface or film is comprised of poly(DL-lactide-co-glycolide) (PLGA), poly(DL-lactide-co-ε-caprolactone) (DLPLCL), poly(ε-caprolactone) (PCL), collogen, gelatin, agarose, poly(methyl methacrylate), galatin/ε-caprolactone, collagen-GAG, collagen, fibrin, PLA, PGA, PLA-PGA co-polymers, poly(anhydrides), poly(hydroxy acids), poly(ortho esters), poly(propylfumerates), poly(caprolactones), poly(hydroxyvalerate), polyamides, polyamino acids, polyacetals, biodegradable polycyanoacrylates, biodegradable polyurethanes and polysaccharides, polypyrrole, polyanilines, polythiophene, polystyrene, polyesters, non-biodegradable polyurethanes, polyureas, poly(ethylene vinyl acetate), polypropylene, polymethacrylate, polyethylene, polycarbonates, poly(ethylene oxide), co-polymers of the above, mixtures of the above, and adducts of the above, or combinations thereof.

In some embodiments, the surface or film is comprised of silicon, titania, zirconia, cobalt-chromium, alumina, silica, barium aluminate, barium titanate, iron oxide, and zinc oxide, nitinol, elastinite, tantalum, elgiloy, phynox, Ti6Al4V, CoCr, TiC, TiN, L605, 316, MP35N, MP20N, stainless steel alloy, 316L stainless steel alloy, 304 stainless steel alloy, or combinations thereof.

In some embodiments, the surface or film further includes a covalently attached bioactive agent. In some embodiments, the nanofibers, nanotubes, or microwells further include an agent to facilitate cell adhesion and cell growth selected from the group consisting of laminin, fibrin, fibronectin, proteoglycans, glycoproteins, glycosaminoglycans, chemotactic agents, and growth factors. In some embodiments, the bioactive agent is selected from a polypeptide, growth factor, a steroid agent, an antibody therapy, an antibody fragment, a DNA, an RNA, and siRNA, an antimicrobial agent, an antibiotic, an antiretroviral drug, an anti-inflammatory compound, an antitumor agent, anti-angiogeneic agent, and a chemotherapeutic agent.

In some embodiments, the nanofibers or nanotubes range in length from about 1 µm to about 500 µm, such as from about 1 µm to about 70 µm. In some embodiments, the nanofibers or nanotubes range in diameter from about 3 nm to about 300 nm. In some embodiments, the nanotubes have a pore diameter range from about 3 nm to about 250 nm. In some embodiments, the surface or film comprises nanofibers at a density greater than 100,000,000 nanofibers per square centimeter. In some embodiments, the surface or film comprises nanotubes at a density greater than 10,000,000 nanotubes per square centimeter. In some embodiments, the surface or film comprises nanofibers at a density greater than 25,000,000 nanofibers per square centimeter, wherein said density provides for an extracellular matrix compatible tissue adhesive. In some embodiments, the surface or film comprises nanotubes at a density greater than 25,000,000 nanotubes per square centimeter, wherein said density provides for an extracellular matrix compatible tissue adhesive.

In some embodiments, the said surface or film ranges in thickness from about 1 μm to about 2.5 mm, such as from about 1 μm to about 750 μm, including from about 1 μm to about 200 μm, and from about 1 μm to about 150 μm.

In some embodiments, the microwells range in diameter from about 1 μm to about 150 μm. In some embodiments, the microwells range in diameter from about 1 μm to about 150 μm. In some embodiments, the surface or film comprises microwells at a density greater than 150,000 microwells per square centimeter.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
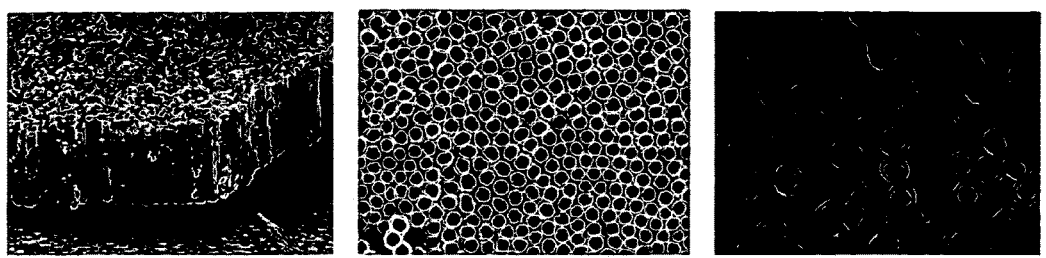
FIG. 1 is a series of SEM images of titania nanotubular surfaces. The left panel shows a cross-sectional view of a mechanically fractured sample; the center panel is a top view of nanotubular surface; and the right panel is a high magnification top view of nanotubular surface. The nanotubes are approximately 80 nm in diameter and 400 nm long.

The present invention provides compositions including a surface or film comprising nanofibers, nanotubes, or microwells, comprising a bioactive agent for elution to the surrounding tissue upon placement in a subject. The compositions are useful as medical implants, including orthopedic implants, dental implants, cardiovascular implants, neurological implants, neurovascular implants, gastrointestinal implants, muscular implants, and ocular implants. The present invention also provides methods of treating a patient in need of such an implant.

Before the present Invention described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the compound" includes reference to one or more compounds and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Introduction

The present invention is based on the observation that nanotubular surfaces provide a favorable template for bone cell growth and differentiation and supported higher cell adhesion, proliferation and viability, while not causing adverse immune response under in vivo conditions. The biocompatibility of metal-oxides has already been proven as the materials have current clinical applications in orthopedic prostheses and dental implants. The inventors have found that osteoblast activity can be significantly enhanced using controlled nanotopographies. Therefore, incorporation of such nanoarchitectures on medical implant surfaces further facilitates the culture and maintenance of differentiated cell states, and promotes long-term osseointegration.

The inventors also found that these nanotubes can be optionally loaded with drugs or biological agents such as proteins. Moreover, the release or elution of the drugs or biological agents from the nanotubes can be controlled by varying the tube length, diameter and wall thickness. By changing the nanotube diameter, wall thickness and length, the release kinetics can be altered for specific drugs in order to achieve sustained release of the drug over a period of time. Thus, these nanotubular surfaces have various potential applications, specifically for implants where faster integration is desired along with controlled release of drugs such as antibiotics or growth factors.

The invention is now described in greater detail.

Methods and Compositions

As noted above, the present invention provides compositions including a surface or film comprising a plurality of nanofibers, nanotubes, or microwells for use in treating a subject in need of a medical implant. In some embodiments, the nanotubes can be optionally be loaded with a bioactive agent for elution to the surrounding tissue upon placement of the implant in a subject. Exemplary medical implants include, but are not limited to, an orthopedic implant, a dental implant, a cardiovascular implant, a neurological implant, a neurovascular implant, a gastrointestinal implant, a muscular implant, an ocular implant, and the like. In some embodiments, the surface or film is a patch that can be used for localized delivery of the bioactive agent to a soft tissue, such as liver, kidney, gastrointestinal tract, pancreas, prostate, colon, and the like. Exemplary bioactive agent include, but are not limited to, polypeptides, nucleic acids, such as DNA, RNA, and siRNA, growth factors, steroid agents, antibody therapies, antimicrobial agents, antibiotics, antiretroviral drugs, anti-inflammatory compounds, antitumor agents, anti-angiogeneic agents, and chemotherapeutic agents. In certain embodiments, the surface or film further includes a covalently attached bioactive agent. In some embodiments, surface or film further includes cells, such as stem cells, retinal progenitor cells, cardiac progenitor cells, osteoprogenitor cells, neuronal progenitor cells, and the like.

In some embodiments, the surface or film expands or unfurls in the presence of a hydrating liquid, such as water present in an insertion site of a subject. By "expands" is meant that surface or film becomes larger in size or volume as a result surrounding liquid hydrating the surface or film. By "unfurl" is meant that the surface or film is unrolled, unfolded, or spread out as a result surrounding liquid hydrating the surface or film Exemplary surfaces and films can be fabricated from a variety of suitable materials that provide the ability to form the desired plurality of nanotubes, nanofibers, and microwells. Exemplary materials include, but are not limited to, biodegradable or bioerodible polymer, such as poly(DL-lactide-co-glycolide) (PLGA), poly(DL-lactide-co-ϵ-caprolactone) (DLPLCL), or poly(ϵ-caprolactone) (PCL), as well as natural biodegradable polymers, such as collagen, gelatin, agarose, and the like. PLGA is a bulk-eroding copolymer of polylactide (PLA) and polyglycolide (PGA), where the ingress of water is faster than the rate of degradation. In this case, degradation takes place throughout the whole of the polymer sample, and proceeds until a critical molecular weight is reached, at which point degradation products become small enough to be solubilized. At this point, the structure starts to become significantly more porous and hydrated. The combination of fast-resorbing PGA and slow-resorbing PLA allows PLGA copolymers to have a resorption rate of approximately 6 weeks. Fast-resorbing PLGA polymers display high shrinkage, which may not present a stable substrate for cells to lay down extracellular matrix. In addition, the production of acidic degradation species by fast-resorbing polymers can compromise tissue repair.

In addition, the surface or film can be fabricated from a variety of suitable metal oxides selected from the group consisting of alumina, titania, Ti6Al4V, nickel, zirconia, cobalt-chromium (CoCr), alumina, silica, barium aluminate, barium titanate, iron oxide, and zinc oxide, as well as shape memory alloys, such as nitinol, or combinations thereof. In certain embodiments, the nanotubes are fabricated of titania. In addition, other examples of suitable metal or metal alloys include, but are not limited to: stainless steels (e.g., 316, 316L or 304), nickel-titanium alloys including shape memory or superelastic types (e.g., nitinol or elastinite); inconel; noble metals including copper, silver, gold, platinum, palladium and iridium; refractory metals including Molybdenum, Tungsten, Tantalum, Titanium, Rhenium, or Niobium; stainless steels alloyed with noble and/or refractory metals; magnesium; amorphous metals; plastically deformable metals (e.g., tantalum); nickel-based alloys (e.g., including platinum, gold and/or tantalum alloys); iron-based alloys (e.g., including platinum, gold and/or tantalum alloys); cobalt-based alloys (e.g., including platinum, gold and/or tantalum alloys); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; platinum-iridium alloys; platinum-tungsten alloys; magnesium alloys; titanium alloys (e.g., TiC, TiN); tantalum alloys (e.g., TaC, TaN); L605; bioabsorbable materials, including magnesium; or other biocompatible metals and/or alloys thereof. Preferably, the implantable frame comprises a self-expanding nickel titanium (NiTi) alloy material, stainless steel or a cobalt-chromium alloy. The nickel titanium alloy sold under the tradename Nitinol.

In some embodiments, at least a subset of the plurality of nanofibers, nanotubes, or microwells further include an erodible capping film to provide for delayed elution of the bioactive agent to the surrounding tissue upon placement of the implant in a subject. For example, the surface or film will include a first subset of nanotubes including a bioactove agent and a second subset of nanotubes including a bioactive agent and capped with an erodible capping film. In such an example, the first subset of nanotubes lacking the erodible capping film will elute the bioactive agent upon placement in the subject, thereby providing early release of the bioactive agent. Over time, as the capping film over the second subset of nanotubes erodes, the bioactive agent will be released. As a result, the combination of capped and uncapped structures provides for two elution profiles, a first early elution from the uncapped subset and a second later elution following erosion of the capping film from the second capped subset.

In certain embodiments, the surface or film includes a plurality of at least two of nanofibers, nanotubes, and microwells, wherein one of said nanofibers, nanotubes, and microwells further include an erodible capping film to provide for delayed elution of said bioactive agent to the surround tissue upon placement of the implant in a subject. For example, the surface or film will include a plurality nanotubes and a plurality of microwells, wherein include a bioactove agent and either the nanotubes or microwells further include an erodible capping film. In such an example, the structure lacking the erodible capping film will elute the bioactive agent upon placement in the subject, thereby providing early release of the bioactive agent. Over time, as the capping film over the capped structure erodes, the bioactive agent will be released. As a result the combination of capped and uncapped structures provides for two elution profiles, a first early elution from the uncapped structures and a second later elution following erosion of the capping film from the second capped structure.

In general, the nanotubes or nanofibers are fabricated to have a diameter ranging from about 3 nm to about 300 nm, including about 10 nm to about 250 nm, about 20 nm to about 225 nm, about 30 nm to about 200 nm, about 50 nm to about 190 nm, about 60 nm to about 180 nm, about 70 nm to about 170 nm, about 80 nm to about 160 nm, and about 90 nm to about 150 nm. In some embodiments, the nanofibers are fabricated at a density greater than at least about 100,000,000 nanofibers per square centimeter or more, including at least about 200,000,000 nanofibers per square centimeter, and at least about 300,000,000 nanofibers per square centimeter. In some embodiments the nanotubes are fabricated at a density greater than at least about 10,000,000 nanotubes per square centimeter, including at least about 25,000,000 nanotubes per square centimeter, and at least about 50,000,000 nanotubes per square centimeter. In some embodiments, the nanofibers and nanotubes are fabricated at a density greater than at least about 25,000,000 nanofibers per square centimeter or more, including at least about 50,000,000 nanofibers per square centimeter, and at least about 75,000,000 nanofibers per square centimeter, wherein the density provides for an extracellular matrix compatible tissue adhesive.

In general, the nanotubes or nanofibers are fabricated to have a length ranging from about 11 µm to about 500 µm, including about 2 µm to about 450 µm, about 3 µm to about 400 µm, about 4 µm to about 350 µm, about 5 µm to about 300 µm, about 6 µm to about 250 µm, about 7 µm to about 200 µm, about 8 µm to about 100 µm, about 9 µm to about 90 µm, about 10 µm to about 18 µm, about 11 µm to about 70 µm, about 12 µm to about 60 µm, about 13 µm to about 50 µm, about 14 µm to about 40 µm, about 15 µm to about 30 µm, and about 16 µm to about 20 µm. In an exemplary embodiment, the nanotubes have a length of about 10 µm.

In general, the nanotubes are fabricated to have pores range in diameter from about 3 nm to about 250 nm, including 4 nm to about 225 nm, including 5 nm to about 200 nm, including 6 nm to about 175 nm, including 7 nm to about 150 nm, including 8 nm to about 125 nm, including 9 nm to about 100 nm, including 10 nm to about 75 nm, including 11 nm to about 70 nm, including 12 nm to about 65 nm, including 13 nm to about 60 nm, including 14 nm to about 50 nm, including 15 nm to about 45 nm, about 20 nm to about 40 nm, about 22 nm to about 38 nm, about 24 nm to about 36 nm, about 26 nm to about 34 nm, about 28 nm to about 32 nm, and about 29 nm to about 31 nm. In an exemplary embodiment, the pores have in diameter of about 20 nm to about 40 nm.

In general, the microwells are fabricated to have a diameter ranging from about 1 µm to about 150 µm, including about 2 µm to about 125 µm, about 3 µm to about 100 µm, about 4 µm to about 80 µm, about 5 µm to about 60 µm, about 6 µm to about 50 µm, about 7 µm to about 40 m, about 8 µm to about 30 µm, and about 7 µm to about 20 µm. In some embodiments, the microwells are fabricated to have a diameter ranging from about 1 µm to about 12 µm. In some embodiments, the microwells are fabricated at a density greater than at least about 150,000 microwells per square centimeter or more, including at least about 200,000 microwells per square centimeter, and at least about 300,000 microwells per square centimeter.

In general, the surface or film is fabricated to have a thickness ranging from about 1 µm to about 2.5 mm, including about 2 µm to about 2 mm, about 3 µm to about 1.5 mm, about 3 µm to about 1 mm, about 4 µm to about 750 µm, and about 5 µm to about 600 µm. In certain embodiments, the surface or film have a thickness ranging from about 1 µm to about 200 µm, including about 3 µm to about 150 µm, about 4 µm to about 100 µm, about 5 µm to about 80 µm, about 6 µm to about 70 µm, about 7 µm to about 60 µm, about 8 µm to about 50 µm, about 9 µm to about 40 µm, and about 10 µm to about 30 µm. In an exemplary embodiment, the surface or film has a thickness of about 150 µm.

In certain embodiments, the surface or film further includes advantageous biological agents and additives to impart, for example, additional osteoinductive and osteoconductive properties to the surface-modified implants. In further embodiments, the advantageous biological agents and additives are added to the nanotubes, nanowires, or microwells for elution to the surrounding tissue upon placement of the implant in the patient. This may be particularly useful for implants of the present invention that are bone implants. In an exemplary embodiment, one or more biological agents or additives may be added to the implant before implantation. The biological agents and additives may be adsorbed onto and incorporated into the surface or film comprising nanotubes, nanowires, or microwells, by dipping the implant into a solution or dispersion containing the agents and/or additives, or by other means recognized by those skilled in the art. In some embodiments, the nanotubes, nanowires, or microwells will release the adsorbed biological agents and additives in a time-controlled fashion. In this way, the therapeutic advantages imparted by the addition of biological agents and additives may be continued for an extended period of time. It may be desirable to include certain additives in the electrolyte solution used during the electrochemical anodization process in order to increase the adsorptive properties of the nanotubes formed on the surface-modified implant. For example, the inclusion of salts in the electrolyte solution used during the electrochemical anodization process may result in the incorporation of ionic substances into the nanotubes, nanowires, or microwells formed on the surface or film. The inclusion of ionic substances in the nanotubes, nanowires, or microwells may impart greater adsorptive properties to the nanotubes due to the polar interactions between the nanotubes, nanowires, or microwells containing ionic substances and the biological agents and additives.

The biological agents or additives may be in a purified form, partially purified form, recombinant form, or any other form appropriate for inclusion in the surface-modified medical implant. It is desirable that the agents or additives be free of impurities and contaminants. Exemplary agents to facilitate cell adhesion and cell grow include laminin, fibrin, fibronectin, proteoglycans, glycoproteins, glycosaminoglycans, chemotactic agents, and growth factors, and the like.

For example, growth factors may be included in the surface-modified implant or to the nanotubes for elution to the surrounding tissue upon placement of the implant in the patent to encourage bone or tissue growth. Non-limiting examples of growth factors that may be included are platelet derived growth factor (PDGF), transforming growth factor b (TGF-b), insulin-related growth factor-I (IGF-I), insulin-related growth factor-II (IGF-II), fibroblast growth factor (FGF), beta-2-microglobulin (BDGF II), and bone morphogenetic factors. Bone morphogenetic factors are growth factors whose activity is specific to bone tissue including, but not limited to, proteins of demineralized bone, demineralized bone matrix (DBM), and in particular bone protein (BP) or bone morphogenetic protein (BMP). Osteoinductive factors such as fibronectin (FN), osteonectin (ON), endothelial cell growth factor (ECGF), cementum attachment extracts (CAE), ketanserin, human growth hormone (HGH), animal growth hormones, epidermal growth factor (EGF), interleukin-1 (IL-1), human alpha thrombin, transforming growth factor (TGF-beta), insulin-like growth factor (IGF-1), platelet derived growth factors (PDGF), and fibroblast growth factors (FGF, bFGF, etc.) also may be included in the surface-modified implant.

Still other examples of biological agents and additives that may be incorporated in the nanotopography of the medical implant are biocidal/biostatic sugars such as dextran and glucose; peptides; nucleic acid and amino acid sequences such as leptin antagonists, leptin receptor antagonists, and antisense leptin nucleic acids; vitamins; inorganic elements; co-factors for protein synthesis; antibody therapies, such as Herceptin®, Rituxan®, Myllotarg®, and Erbitux®; hormones; endocrine tissue or tissue fragments; synthesizers; enzymes such as collagenase, peptidases, and oxidases; polymer cell scaffolds with parenchymal cells; angiogenic agents; antigenic agents; cytoskeletal agents; cartilage fragments; living cells such as chondrocytes, bone marrow cells, mesenchymal stem cells, natural extracts, genetically engineered living cells, or otherwise modified living cells; autogenous tissues such as blood, serum, soft tissue, and bone marrow; bioadhesives; periodontal ligament chemotactic factor (PDLGF); somatotropin; bone digestors; antitumor agents and chemotherapeutics such as cis-platinum, ifosfamide, methotrexate, and doxorubicin hydrochloride; immuno-suppressants; permeation enhancers such as fatty acid esters including laureate, myristate, and stearate monoesters of polyethylene glycol; bisphosphonates such as alendronate, clodronate, etidronate, ibandronate, (3-amino-1-hydroxypropylidene)-1,1-bisphosphonate (APD), dichloromethylene bisphosphonate, aminobisphosphonatezolendronate, and pamidronate; pain killers and anti-inflammatories such as non-steroidal anti-inflammatory drugs (NSAID) like ketorolac tromethamine, lidocaine hydrochloride, bipivacaine hydrochloride, and ibuprofen; antibiotics and antiretroviral drugs such as tetracycline, vancomycin, cephalosporin, erythromycin, bacitracin, neomycin, penicillin, polymycin B, biomycin, chloromycetin, streptomycin, cefazolin, ampicillin, azactam, tobramycin, clindamycin, gentamicin, and aminoglycocides such as tobramycin and gentamicin; and salts such as strontium salt, fluoride salt, magnesium salt, and sodium salt.

Examples of antimicrobial agents include, but are not limited to, tobramycin, amoxicillin, amoxicillin/clavulanate, amphotericin B, ampicillin, ampicillin/sulbactam, atovaquone, azithromycin, cefazolin, cefepime, cefotaxime, cefotetan, cefpodoxime, ceftazidime, ceftizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscarnet, ganciclovir, atifloxacin, imipenem/cilastatin, isoniazid, itraconazole, ketoconazole, metronidazole, nafcillin, nafcillin, nystatin, penicillin, penicillin G, pentamidine, piperacillin/tazobactam, rifampin, quinupristin-dalfopristin, ticarcillin/clavulanate, trimethoprim/sulfamethoxazole, valacyclovir, vancomycin, mafenide, silver sulfadiazine, mupirocin, nystatin, triamcinolone/nystatin, clotrimazole/betamethasone, clotrimazole, ketoconazole, butoconazole, miconazole, and tioconazole.

Antiangiogenic agents include, but are not limited to, interferon-α, COX-2 inhibitors, integrin antagonists, angiostatin, endostatin, thrombospondin-1, vitaxin, celecoxib, rofecoxib, JTE-522, EMD-121974, and D-2163, FGFR kinase inhibitors, EGFR kinase inhibitors, VEGFR kinase inhibitors, matrix metalloproteinase inhibitors, marmiastat, prinomastat, BMS275291, BAY12-9566, neovastat, rhuMAb VEGF, SU5416, SU6668, ZD6474, CP-547, CP-632, ZD4190, thalidomide and thalidomide analoges, sqalamine, celecoxib, ZD6126, TNP-470, and other angiogenesis inhibitor drugs.

In general, the bioactive agent eluting nanotubes, nanowires, or microwells will elute the bioactive agent to the surrounding tissue upon placement of the implant in the patient for a period raging from about 2 minutes to about 3 months or more, including 5 minutes to about 14 weeks, such as about 24 hours, 72 hours, about 3 days, about 7 days, about 2 weeks, about 3 weeks, about 4 weeks, about 6 weeks, about 8 weeks, about 12 weeks, or more.

In further embodiments, in which is desirable to modulate the release kinetics of the bioactive agents that is eluted from the nanotubes, nanowires, or microwells a suitable synthetic or natural polymer is combined with the bioactive agent prior to or at the same time the nanotubes, nanowires, or microwells are loaded with the bioactive agent. Suitable synthetic and natural polymers include, but are not limited to, biodegradable or bioerodible polymers, such as poly(DL-lactide-co-glycolide) (PLGA), poly(DL-lactide-co-ε-caprolactone) (DLPLCL), or poly(ε-caprolactone) (PCL), collagen, gelatin, agarose, and other natural biodegradable materials.

The mineral nanotubes, nanowires, or microwells surfaces with or without adhesion-promoting peptides and/or other biological agents, can be compacted and/or structured and used alone to form an implant. Alternatively, a structured substrate can be coated with a composition comprising the nanotubes, nanowires, or microwells with or without adhesion-promoting peptides. Substrates include any conventional substrates for medical implants or for other types of implants known in the art.

Also provided is a method of treating a patient in need of a medical implant comprising the steps of selecting the medical implant wherein the implant comprises nanotubue, nanowires, or microwells coated surface and placing the implant into the patient. Exemplary implants include, orthopedic implants, dental implants, cardiovascular implants, such as a pacemaker, neurological implants, neurovascular implants, gastrointestinal implants, muscular implants, ocular implants, and the like. In this embodiment of the invention the term "selecting" means, for example, purchasing, choosing, or providing the implant rather than preparing the implant.

The method of the present invention can be used for both human clinical medicine and veterinary applications. Thus, the patient can be a human or, in the case of veterinary applications, can be a laboratory, agricultural, domestic, or wild animal. The present invention can be applied to animals including, but not limited to, humans, laboratory animals such as monkeys and chimpanzees, domestic animals such as dogs and cats, agricultural animals such as cows, horses, pigs, sheep, goats, and wild animals in captivity such as bears, pandas, lions, tigers, leopards, elephants, zebras, giraffes, gorillas, dolphins, and whales.

In another embodiment, a method for enhancing osseointegration of an orthopedic implant is provided. The method comprises the steps of selecting the orthopedic implant wherein the implant comprises nanotubue, nanowires, or microwells coated surface and placing the implant into a patient. In this embodiment of the invention the term "selecting" means, for example, purchasing, choosing, or providing the implant rather than preparing the implant. The patient can be a human or, in the case of veterinary applications, can be a laboratory, agricultural, domestic, or wild animal.

Enhancement of osseointegration is increased osseointegration compared to that obtained with conventional implant materials. Enhanced osseointegration can be demonstrated by increased osteoblast adhesion, increased osteoblast proliferation, increased calcium deposition, enzyme activity assays, or by any other art-recognized technique used to detect osseointegration.

In yet another embodiment a method of preparing a medical implant is provided. The method comprises the step of forming a composition comprising nanotubes, nanowires, or microwells. The method can further comprise the step of coating a substrate with the nanotube, nanowire, or microwell-containing composition. The composition formed can be a composition containing the nanotubes, nanowires, or microwells alone, a nanocomposite composition, a nanocomposite composition containing an adhesion-promoting peptide, or any other composition containing nanotubes, nanowires, or microwells that is suitable for use in accordance with the present invention.

Kits

Kits for use in connection with the subject invention are also provided. The above-described surface or film comprising nanofibers, nanotubes, or microwells, comprising a bioactive agent for elution to the surrounding tissue upon placement in a subject, as well as medical implants including the surface or film, can be provided in kits, with suitable instructions in order to conduct the methods as described above. The kit will normally contain in separate containers the nanotubes or materials necessary for fabricating the nanotubular coating on a surface. Instructions (e.g., written, tape, VCR, CD-ROM, etc.) for carrying out the methods usually will be included in the kit. The kit can also contain, depending on the particular method, other packaged reagents and materials (i.e. buffers and the like).

The instructions are generally recorded on a suitable recording medium. For example, the instructions may be printed on a substrate, such as paper or plastic, etc. As such, the instructions may be present in the kits as a package insert, in the labeling of the container of the kit or components thereof (e.g., associated with the packaging or sub-packaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed from or from where the instructions can be downloaded.

Still further, the kit may be one in which the instructions are obtained are downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following methods and materials were used in the Examples below.

Fabrication of Titania Nanotubular Surfaces

Titania nanotubular surfaces were fabricated using an anodization process described elsewhere (Mor et al., Advanced Functional Materials 2005, 15:1291-96; Varghese et al., Journal of Materials Research 2003, 18:156-155). In brief, titanium foils (Alfa Aesar) of thickness 0.25 mm and 99.8% purity were used to fabricate titania nanotubes. The electrolyte consisted of 0.5 vol % hydrofluoric acid (J. T. Baker) in water, and a platinum (Alfa Aesar) electrode served as a cathode. Anodization was performed at a constant voltage of 20V for 45 mins. The samples were cleaned using deionized water after completing the anodization process. The nanotubes were then sintered at 500° C. in dry oxygen as it is known that these ambients influence the phase transformation of titania. The surface morphologies of the samples were studied using a Sirion Scanning Electron Microscope (SEM).

Isolation and Culture of Marrow Stromal Cells (MSC)

Male Lewis rats were obtained from the Laboratory of Animal Resource Center (LARC) at University of California, San Francisco. The animals were euthanized according to an IACUC approved protocol. Limbs were removed aseptically and placed in cold phosphate buffer solution (PBS) in 50 ml falcon tubes. Bones were dissected from the soft tissues under a cell culture hood. Metaphyseal ends of the bones were removed to allow access to the marrow cavity. The contents of marrow cavity were flushed out using a 25-gauge needle attached to a 10 ml syringe containing alpha-modified MEM (αMEM) supplemented with 10% FBS and 1% penn/strep. The flushed cell suspension was then filtered through a 70 μm nylon strainer. In order to seed cells on nanotubular surfaces (1 cm×1 cm), surfaces were adhered to the bottom of 12-well plates with medical-grade silicone (Dow) and cured overnight. The plates were then placed under ultraviolet light in a biological hood for 30 mins. Before seeding the cells, the surfaces were soaked in 70% ethanol for 30 minutes for sterilization. The surfaces were then washed twice with warm PBS and the cells were plated at a density of 5×106 per well. On day 4 of culture, half of the media was removed and replaced with fresh αMEM supplemented with 10% FBS and 1% penn/strep. On day 7 of culture, all media was removed and cells were supplied with the complete media. The complete Media includes αMEM supplemented with 10% FBS, 1% Penn/Strep, Dexamethasone (10-8M final concentration), Ascorbic acid (50 μg/ml final) and beta-glycerol phosphate (8 mmol final). Media was then changed every two days for the duration of the experiment. Cell response was investigated in two stages; (a) cell adhesion and proliferation up to 7 days after the initial culture phase and (b) cell differentiation for up to 3 weeks after providing complete media (i.e. after 7 days of initial culturing). Commercially available titanium and tissue culture polystyrene were used as standards.

MSC Adhesion and Proliferation

MSC adhesion was investigated 1 day after seeding the cells and proliferation was investigated after days 4 and 7. The adhered and proliferated cells were quantified by trypsinizing the cells on surfaces and counting them using a hemacytometer.

Cell Viability

The cell viability was investigated 4 days after seeding the cells using a commercially available MTT assay (Sigma). The MTT method is simple, accurate and yields reproducible results. The key component is (3-[4,5-dimethylthiazol-2-yl]-2,5-diphenyl tetrazolium bromide) or MTT. Solutions of MTT, dissolved in medium or balanced salt solutions without phenol red, are yellowish in color. Mitochondrial dehydrogenases of viable cells cleave the tetrazolium ring, yielding purple formazan crystals. The standard protocol provided with the MTT kit was followed. The resulting purple solution was spectrophotometrically measured at 570 nm using a spectrophotometer. An increase or decrease in cell number resulted in a concomitant change in the amount of formazan formed, indicating the degree of cytotoxicity caused by the surfaces.

Calcein Staining

After 7 days of culture, the cells on the surfaces were stained with calcein. The polyanionic dye calcein is well retained within live cells, thus producing an intense uniform green fluorescence in live cells. The surfaces were washed twice with PBS before staining. They were incubated in 2 μM solution of calcein for 30-45 mins. The surfaces were imaged using a fluorescence microscope after washing with PBS.

Total Intracellular Protein Content

Total protein content of MSCs is extremely important since it is the indication of healthy growth and normal cell response on nanotubular environments. Thus, the amount of protein produced by cells was measured up to 3 weeks of culture after providing complete media. In order to release the intracellular protein, the adhered cells on the substrates were lysed in deionized water using a standard four cycle freeze-thaw method. The resulting lysate solution was then used for analysis. The total protein content was determined by a BCA (bicinchoninic acid) assay kit (Pierce) and the absorbance of the solution was measured using a spectrophotometer at a wavelength of 570 nm. The absorbance was then converted to protein content using an albumin standard curve to determine the amount of intracellular protein.

Alkaline Phosphatase Activity

ALP activity is an important parameter to access the normal functionality of cells on a surface; hence the activity was measured up to 3 weeks after providing complete media. The resulting lysate solution was used to measure the ALP activity using a commercially available colorimetric assay (Teco). The absorbance of the solution was measured using a spectrophotometer at a wavelength of 590 nm. The absorbance was then converted to concentration using ALP standard and all the data was normalized with total protein content to account for changes in number of cells present on each surface.

Analysis of Calcium Content

The calcium content was measured up to 3 weeks in culture using a colorimetric assay (Teco). After the lysate was removed; the surfaces were soaked overnight in 6N HCl solution to dissolve the deposited calcium. The calcium solution was then reacted with assay reagents and the absorbance of the solution was measured photometrically at 570 nm. The absorbance was then converted to concentration using calcium standards and all the data was normalized with total protein content to account for changes in the number of cells present on each surface.

Extracellular Matrix Production

Calcium and phosphorus are the primary components of bone matrix. If cells have differentiated on the surfaces, they will begin to deposit bone matrix. In order to detect the presence of calcium and phosphorus on our surfaces, the samples were air dried for XPS analysis. XPS is a surface sensitive technique and detects trace levels of elements present on the surface. Survey spectra were collected from 0 to 1100 eV using a SSI S-Probe Monochromatized XPS Spectrometer with Al-Kα-X-ray small spot source (1486.6 eV) and multichannel detector with a pass energy of 160 eV. Data for percent atomic composition and atomic ratios for deposited calcium and phosphorous on alumina surfaces for up to three weeks of culture were calculated from the survey scans using the manufacturer supplied software.

Cell Morphology

Cell morphology on nanotubular and control surfaces was examined using SEM. The surfaces were imaged after 1, 4 and 7 days of culture to investigate the adhesion and proliferation stage; and after 1, 2 and 3 weeks of culture after providing complete media. Prior to imaging, the cells were fixed and dehydrated. The surfaces were rinsed twice in PBS and then soaked in the primary fixative of 3% glutaraldehyde (Sigma), 0.1M of sodium cacodylate (Polysciences), and 0.1M sucrose (Sigma, ST. Louis Mo.) for 45 minutes. The surfaces were subjected to two five-minute washes with a buffer containing 0.1M sodium cacodylate and 0.1M sucrose. The cells were then dehydrated by replacing the buffer with increasing concentrations of ethanol (35, 50, 70, 95 and 100%) for ten minutes each. Further, the cells were dried by replacing ethanol by hexamethyldisilazane (HMDS) (Polysciences) for 10 minutes. The HMDS was removed, and the surfaces were air dried for 30 minutes. SEM imaging was conducted on the Sirion Scanning Electron Microscope at voltages ranging from 10-20 kV after the surfaces were sputter coated in gold. The sputter coater was set at current of 20 mA and pressure of 0.05 mbar for twenty seconds to deposit a 10 nm layer of gold.

In Vivo Immune Response of Titania Nanotubular Surfaces

Two male Lewis rats, about 225 gm, were anesthetized in an induction box with 3% isoflurane and then kept on 1.5% isoflurane on a fitted nose mask during the course of the surgery. Animals were clipped and prepped following aseptic techniques described in the guidelines by IACUC. A 1 cm midline incision was made in the scruff region of the neck. The sample implant discs (5 mm diameter and 1 mm thick) were sterilized by autoclaving. The skin layer was detached from the muscle layer forming a pocket on each side of the incision, were the surfaces were placed. Two samples were implanted in each animal making a total of 4 samples (2 nanotubular titania and 2 titania control). The skin layer was then sutured with 4.0 nylon suture. The animals were allowed to recover before being returned to the animal facility. They were monitored every day for the first week and twice a week thereafter until 4 weeks. Nylon stitches were removed after a week. After 4 weeks, the animals were anesthetized as described above. A midline incision was made in the scruff region of the neck Skin layer was lifted to expose the implants which were then retrieved together with the surrounding tissue. The animals were then sacrificed by cardiac removal.

Directly after euthanasia, retrieved implants with the surrounding tissues were fixed in 4% phosphate buffered formaldehyde solution. Subsequently, the specimens were dehydrated and embedded in Spurr's embedding media. After polymerization, sections of 300 µm in thickness containing tissue/implant interface were obtained using a slow-speed diamond saw (Buehler Isomet saw). The sections were then grounded using 400 and 600 grit sand paper on a wheel grinder (Buehler Ecomet III grinder) to a final thickness of 50 µm and stained with haematoxylin and eosin.

Statistical Analysis

Each experiment was reconfirmed at least three times using cells from different marrow stromal preparations. All the results were analyzed using analysis of variance (ANOVA). Statistical significance was considered at $p<0.05$.

Filling of Nanotubes

The nanotubes were filled via a simplified lyophilization method (Foraker et al. Pharm Res 20(1):110-6 (2003); Salonen et al. J Control Release 108(2-3):362-74 (2005)). In brief, 100 mg/ml of solutions of BSA in PBS (pH 7.1) and LYS in sodium acetate buffer (50 mM, pH 4.5) were prepared. Titania nanotube surfaces (0.5 cm×0.5 cm) were cleaned with deionized water prior to loading of BSA and LYS. 1 µL of protein solution was pipetted onto the nanotube surface and gently spread to ensure even coverage. The surfaces were then allowed to dry under vacuum at room temperature for 2 hours. After drying, the loading step was repeated until the appropriate amount of protein was present in the nanotube array. In this way the surfaces were loaded with 200, 400 and 800 µg of protein. After the final drying step, the surfaces were rinsed quickly by pipetting 500 µl of PBS over the surface to remove any excess protein on the surface. The rinse solutions were collected and stored for further analysis. Nanotube surfaces adsorbed with the same concentration of protein were used as controls. The adsorption was carried out by incubating the surfaces for 20 minutes followed by rinsing with PBS.

X-Ray Photoelectron Spectroscopy

To evaluate the differences in amounts of protein in nanotubes, X-ray photoelectron spectroscopy (XPS) analysis was carried out. XPS is a surface sensitive technique which can detect changes in surface composition for up to 2-20 atomic layers, depending on the material. Since the nanotubes are approximately 400 nm long, XPS can be used to verify the differences in surface concentrations due to different amounts of BSA and LYS loaded. The loaded nanotube surfaces along with adsorbed surfaces were mounted on an XPS stage. Three spots per sample were analyzed. The analysis was conducted on a SSI S-Probe Monochromatized XPS Spectrometer which uses an Al-Kα-X-ray source (1486.6 eV) with an Omni Focus III small area lens and multichannel detector. A concentric hemispherical analyzer (CHA) was operated in the constant analyzer transmission mode to measure the binding energies of emitted photoelectrons. The binding energy scale was calibrated by the $Au4f_{7/2}$ peak at 83.9 eV, and the linearity was verified by the $Cu3p_{1/2}$ and $Cu2p_{3/2}$ peaks at 76.5 and 932.5 eV respectively. Survey spectra were collected from 0 to 1100 eV with pass energy of 160 eV, and high-resolution C1s spectra were collected for each element detected with pass energy of 10 eV. Survey and high resolution spectra were collected at a 65° take off angle, defined as the angle spanned by the electron path to the analyzer and the sample surface. All spectra were referenced by setting the hydrocarbon C1s peak to 285.0 eV to compensate for residual charging effects. Data for percent atomic composition and atomic ratios were calculated using the manufacturer supplied sensitivity factor.

Release from Nanotubes

In order to release the proteins from the nanotubes, the surfaces were immersed in 500 µl of PBS in a 24-well plate at room temperature with orbital shaking at 70 rpm. 200 µl of samples were taken after specific intervals of time to determine the release kinetics. Samples were collected periodically for up to 120 minutes. The solution was replaced with 200 µl of fresh PBS every time the samples were taken. The samples were analyzed for protein content using a commercially available Micro-BCA assay kit and the concentration was adjusted for dilutions due to replacement of fresh PBS.

Example 1

Fabrication of Nanotubular Surface Coated Implants

The results show development of nanotubular surfaces that can be applied to existing implants, thereby providing a strategy that can be applied quite readily in the clinical environment. The approach to achieving an optimal material nanoarchitecture uses a simple anodization technique to fabricate vertically oriented, immobilized, high-aspect ratio titania nanotube arrays. FIG. 1 shows an SEM image of titania nanotubes with pore size of approximately 80 nm and length of 400 nm prepared using anodization voltage of 20V for 20 mins. It can be seen that the nanotube array is substantially uniform over the substrate surface. There is a precise correlation between the anodization voltage and pore size, thus by varying the voltage and anodization time, substrates with different size scales can be fabricated (Mor et al., Journal of Materials Research 2003, 18(11):2588-93; Rougraff et al., J Bone Joint Surg Am 2002, 84-A(6):921-9). The large surface area of the nanotube-array structure and the ability to precisely tune pore size, wall-thickness, and nanotube length to optimize biotemplating properties are among the many desirable properties of this architecture to use them for orthopedic applications.

The fabricated nanotubular titania surfaces were seeded with marrow stromal cells obtained from male Lewis rats. Bone marrow extracts containing osteoprogenitors combined with various matrices have been shown to accelerate and enhance bone formation within osseous defects when compared with the matrix alone (Rougraff et al., J Bone Joint Surg Am 2002, 84-A(6):921-9; Tiedeman et al., Orthopedics 1995, 18(12):1153-8). MSCs contain a pluripotent population of cells capable of differentiating along multiple mesenchymal lineages (e.g., bone (Haynesworth et al., Bone 1992, 13(1):81-8; Prockop et al., Science 1997, 276(5309): 71-4), ligament (Altman et al., Faseb J 2002; 16(2):270-2), adipose (Beresford et al., J Cell Sci 1992; 102 (Pt 2):341-51), cartilage (Wakitani et al., J Bone Joint Surg Am 1994; 76(4):579-92) and muscle tissue (Seshi et al., Blood Cells Mol Dis 2000; 26(3):234-46)). Because tissue culture techniques allow the isolation and ex vivo expansion of this cell population from animals, these cells represent an ideal osteogenic cell source to be used to evaluate their interaction with nanostructured surfaces. The ability of MSCs to induce bone formation in vivo is believed to be due to the interaction of osteoprogenitors present within the cell populations with osteoinductive factors, such as bone morphogenetic proteins and various growth factors and cytokines, which cause them to differentiate into bone-forming cells i.e. osteoblasts, which will then eventually form bone matrix. Commercially available pure titanium and tissue culture polystyrene were used as controls.

Figure 2:
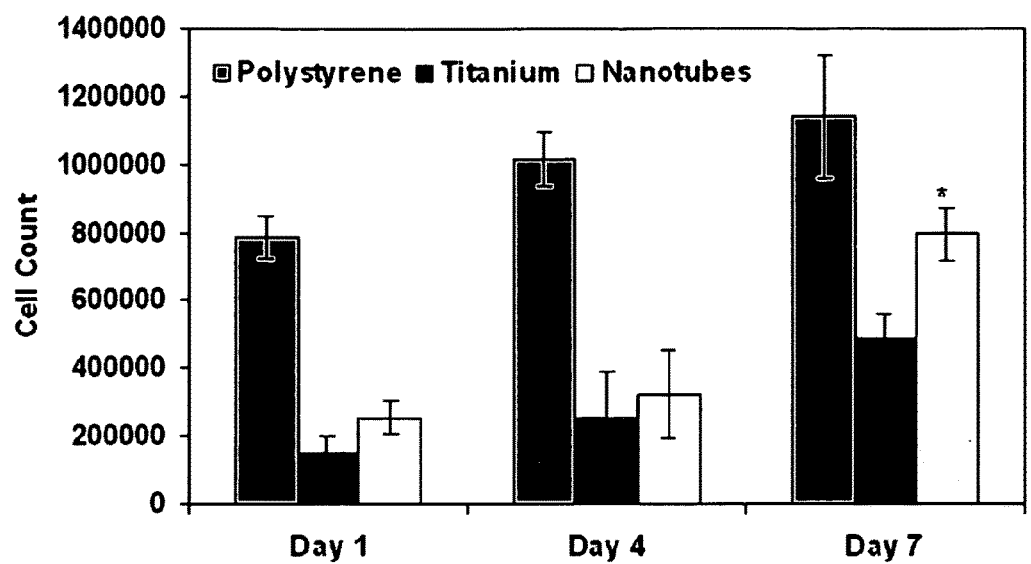
FIG. 2, panel a, shows marrow stromal cell adhesion and proliferation on polystyrene, titanium and nanotubular surfaces for up to 7 days of culture, nanotubular surfaces show approx. 40% more cell proliferation after 7 days of culture compared to titanium surface ($p<0.05$); panel b shows cell viability measured as absorbance using MTT assay after 4 days for cell culture on polystyrene, titanium and nanotubular surface.

Significant attachment to the surfaces is necessary in order for MSCs to spread and differentiate. By determining the initial attachment of MSCs onto the nanotubular surfaces, we can examine the correlation of cell attachment and physical and mechanical properties of the scaffold. Contact and interactions between cells will eventually affect the differentiation process. Thus, cell adhesion and proliferation was investigated on nanotubular titania surfaces; and was compared to that from titanium and polystyrene. FIG. 2, panel a, shows the results of MSC adhesion after 1 day and proliferation after 4 and 7 days of culturing the cells. As, expected, polystyrene supported highest cell adhesion and proliferation. However, the results indicated a 40% increase in the number of cells present on nanotubular titania surfaces compared to flat titania surfaces (p<0.05) after 7 days of culture. The results show that topographical cues at nanoscale level present on the nanotubular titania surfaces promote cell adhesion and proliferation.

Figure 3:
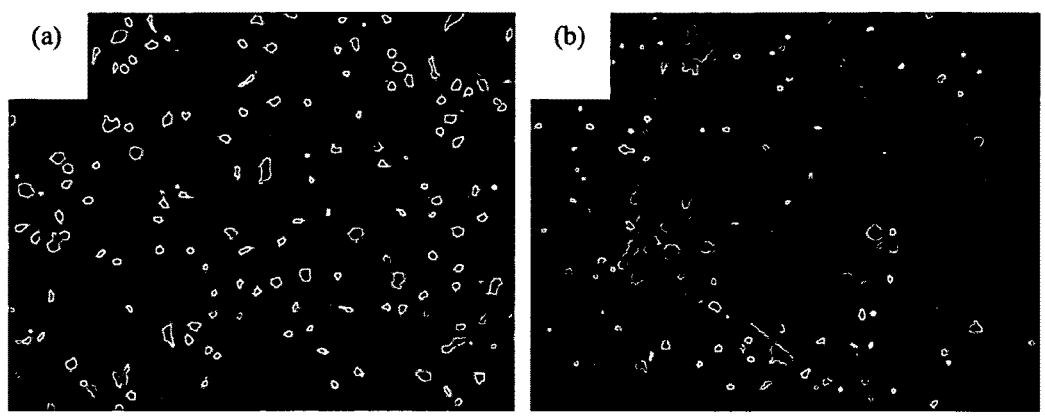
FIG. 3 shows fluorescence microscopy images (10×) of live marrow stromal cells stained with calcein on (panel a) titanium and (panel b) nanotubular surfaces; the cells seem to form clusters on nanotubular surface which is absent on titanium surfaces.

Higher adhesion on the surface does not necessarily suggest that the cells are viable and functional. Therefore, the cell viability was also assessed using the MTT assay. FIG. 2, panel b, shows the absorbance values obtained for cells adhered to surfaces for 4 days. The results show that the cells are viable on nanotubular titania surfaces as well as on titanium and polystyrene surfaces. The absorbance values for nanotubular and titanium surfaces are similar to that obtained from polystyrene. Polystyrene is commonly used as a positive control for cell culture. Hence the similarity between the absorbance values shows that the cells are healthy and viable on all three surfaces. After 7 days of culture (just before providing the complete media), the cells were stained with calcein. Calcein staining is fluorescence based staining method for assessing cell viability. It is a faster, less expensive and more sensitive indicator of cytotoxic events. Live cells are distinguished by the presence of intracellular esterase activity, determined by the enzymatic conversion of the virtually nonfluorescent cell-permeant calcein to the intensely fluorescence calcein. The polyanionic dye calcein is well retained within the live cells, producing uniform green fluorescence in live cells. FIG. 3, panels a and b, shows fluorescence microscopy images of MSCs on titanium and nanotubular surfaces respectively stained with calcein. The images show that the cells are viable on these surfaces after 7 days of culture. Furthermore, closer inspection of cells on nanotubular surfaces reveals the formation of clusters, which is a normal phenotypic behavior of MSCs. This behavior is absent on flat titanium surfaces, showing that the nanotubular surfaces are providing a more favorable microenvironment for MSCs.

Figure 4:
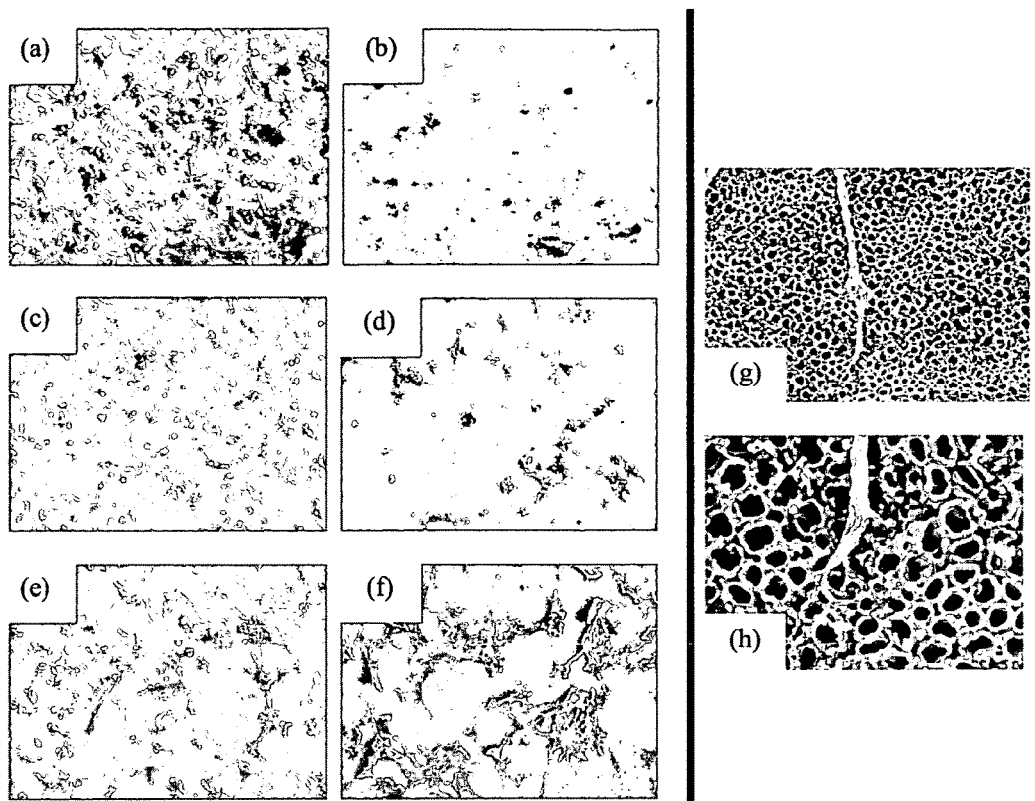
FIG. 4 shows a series of SEM images of marrow stromal cells on titanium and nanotubular surfaces for up to 7 days of culture. Cells show spherical morphology on titanium (panel a) compared to spreading morphology on nanotubular surface (panel b) after 1 day of culture. After 4 days of culture, cells still show spherical morphology on titanium surface (panel c) compared to spreading and clustering morphology on nanotubular surface (panel d). After 7 days of culture, some of the cells on titanium seem to be spreading (panel e), however the cells show high degree of spreading and have started communicating on nanotubular surface (panel f). High magnification SEM image after 7 days of culture (panel g) on nanotubular surface shows that cell extensions are protruding into the nanotubular architecture.

MSC morphology on titanium and nanotubular titania surfaces was investigated using SEM. FIG. 4 shows SEM images of MSCs after 1, 4 and 7 days of culture on titanium and nanotubular surfaces. As expected, the cells are spherical after day 1 on both titanium and nanotubular surfaces (FIG. 4, panels a and b, respectively). After 4 days of culture, the MSCs still show a spherical morphology on titanium surfaces (FIG. 4, panel c); however they show a spreading morphology on nanotubular surfaces (FIG. 4, panel d). By day 7, the MSCs on titanium surfaces are still isolated with minimal spreading (FIG. 4, panel e), whereas the MSCs on nanotubular surfaces have formed a network indicative of cell-cell communication (FIG. 4, panel f). These results show that the MSCs are able to spread faster on nanotubular surfaces as compared to titanium surfaces within 7 days of culture. High magnification SEM images were taken after 7 days on nanotubular surfaces to visualize the cell extensions. FIG. 4, panels g and h show high magnification SEM images of an MSC extension probing the nanotubular architecture. The length of the extension is many times greater then the cell diameter. These extensions help the cell anchor itself to the nanotubular structure. By doing so, the cells can adhere and spread on the surface, resulting in enhanced long term differentiation.

Figure 5:
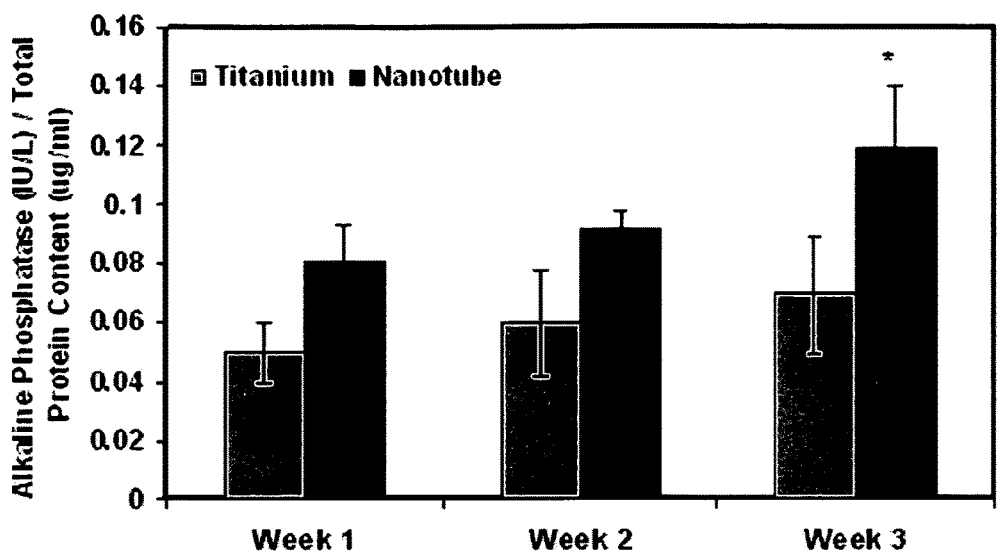
FIG. 5, panel a, is a graph showing ALP activity measured for up to 3 weeks of culture of marrow stromal cells on titanium and nanotubular surface after providing complete media, data normalized with total protein content to account for the effect of different number of cells on each surface, ALP activity is approx. 50% higher after 3 weeks of culture on nanotubular surfaces ($p<0.05$); panel b is a graph showing Calcium concentration measured for up to 3 weeks of culture of marrow stromal cells on titanium and nanotubular surface, data normalized with total protein content to account for the effect of different number of cells on each surface, calcium content is approx. 50% higher after 3 weeks on nanotubular surface ($p<0.05$).
Figure 5:
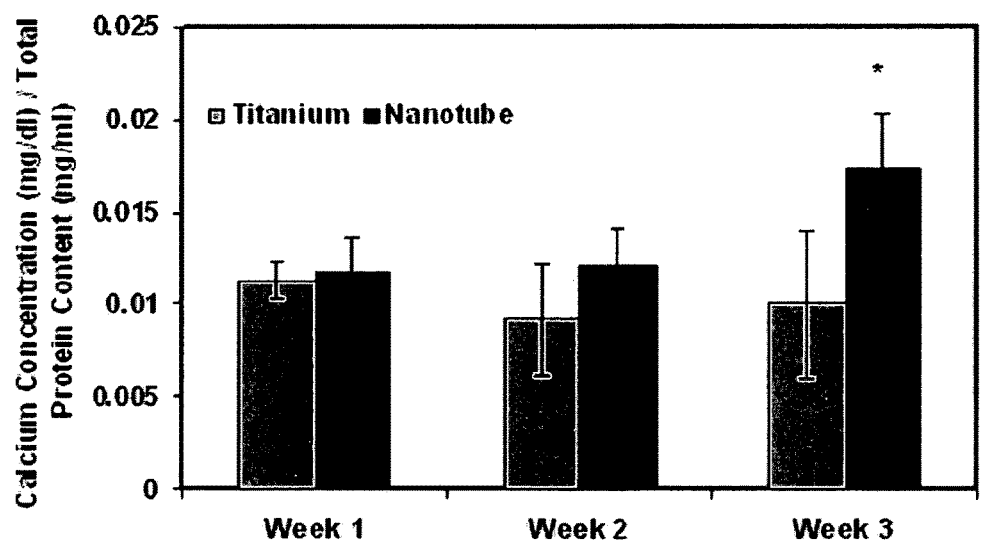

After 7 days of culture on titanium and nanotubular titania surfaces, the MSCs were provided with complete media to initiate differentiation and matrix deposition. Alkaline phosphatase activity (ALP) activity was measured for up to 3 weeks of culture after providing complete media. The ALP levels are age dependent; however the levels are elevated during the period of active bone growth, and thus were measured. A colorimetric assay was used to measure the ALP levels. FIG. 5, panel a shows the ALP activity normalized with total protein content to account for difference in number of cells present on each surface. The cells present on nanotubular surfaces show higher ALP levels compare to those on titanium surfaces. There is approximately a 50% increase in ALP levels on nanotubular surfaces after 3 weeks of culture (p<0.05).

As the cells differentiate, they begin to deposit bone matrix on the surface. The bone matrix predominantly consists of calcium phosphate. Thus, the amount of calcium and phosphorous on the surfaces can be measured using X-ray photoelectron spectroscopy (XPS). XPS is a surface sensitive technique and detect presence of trace amount of elements on the surface. Table 1 shows the ratios of atomic concentrations of calcium and phosphorous to that of titanium obtained by survey scans of titanium and nanotubular surfaces for up to 3 weeks of culture. The results show a steady increase in the amounts of calcium and phosphorous on nanotubular surfaces, compared to a negligible increase on titanium surfaces. This corresponds to greater bone matrix deposition on nanotubular surfaces as compared to titanium surfaces. Furthermore, the calcium deposited on all surfaces was dissolved in hydrochloric acid and its concentration was measured using a colorimetric assay. Calcium reacts with cresolphthalein complexone in 8-hydroxyquinoline to form a purple color which was then measured photometrically. FIG. 5, panel b shows the calcium concentration normalized with respect to total protein content to account for the difference in cell number on each surface. These results closely correlate with the results obtained from XPS. Again, there is approximately 50% increase in calcium content on nanotubular surfaces compared to titanium surfaces for up to 3 weeks of culture ($p<0.05$). These results show that nanotubular surfaces provide a favorable interface for MSC differentiation and matrix production.

TABLE 1

|  | Ca/Ti | | P/Ti | |
| --- | --- | --- | --- | --- |
|  | Titanium | Nanotubes | Titanium | Nanotubes |
| Week 1 | 0.31 | 0.32 | 0.37 | 0.41 |
| Week 2 | 0.32 | 0.56 | 0.42 | 0.78 |
| Week 3 | 0.34 | 1.21 | 0.44 | 1.65 |

Figure 6:
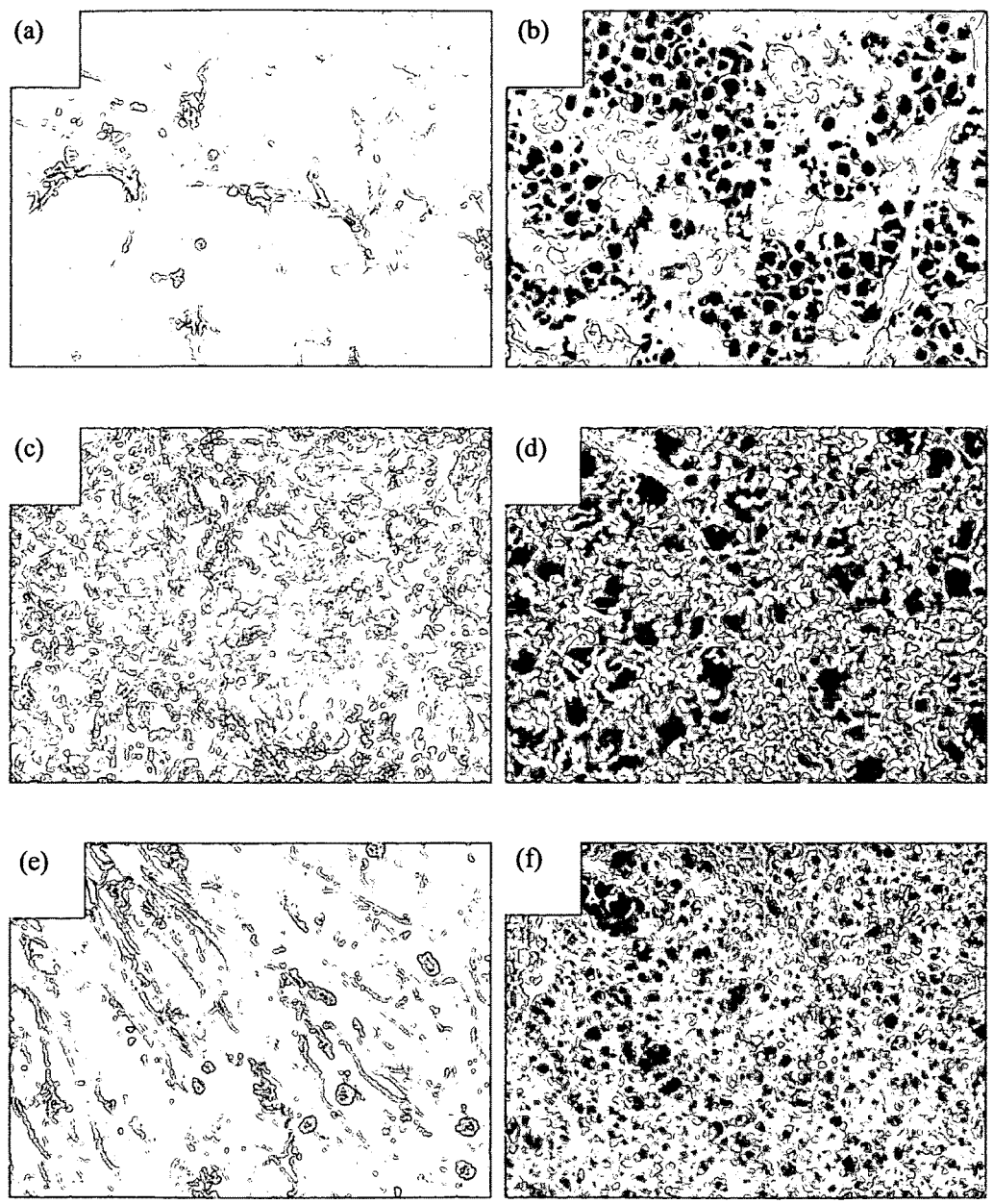
FIG. 6 is a series of SEM images of MSCs on nanotubular surfaces for up to 3 weeks of culture. Formation of cell clusters (panel a) and deposition of granular material (panel b) on nanotubular surfaces after 1 week; After 2 weeks, the surface is almost all covered by cells (panel c) and the nanotubes are further filled with matrix (panel d). After 3 weeks, the entire surface is covered with well spread cells (panel e) and the nanotubes are almost completely filled with matrix constituents (panel f).

The morphology of MSCs during the differentiation phase on nanotubular surfaces was investigated using SEM. FIG. 6 shows SEM images of MSCs on nanotubular surfaces for up to 3 weeks of culture. The cells show a spreading morphology and network formation on the surface after 1 week of culture (FIG. 6, panel a). High magnification SEM images show the presence of granular material on the nanotubular surface (FIG. 6, panel b). After 2 weeks, the SEM images show that the whole surface is covered with a network of well spread cells (FIG. 6 panel c). A close look at the areas surrounding the cells confirms that the nanopores are being filled in with matrix (FIG. 6, panel d). After 3 weeks of culture, the SEM images show that the whole surface is completely covered with both cells and mineralized matrix components (FIG. 6, panel e). Again, a high magnification SEM image of the area around the cells shows that the nanotubular structures are completely filled with a porous material. As discussed earlier, XPS analysis shows that this deposited material predominantly consisted of calcium and phosphorous, important bone matrix constituents.

Figure 7:
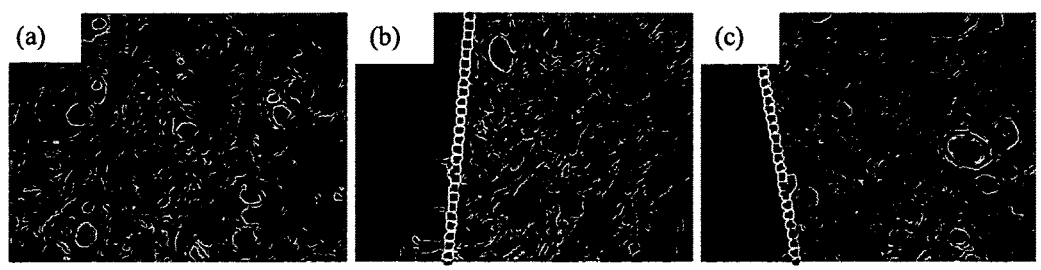
FIG. 7 is a series of images of histological analysis of tissue (panel a) control—normal healthy tissue; (panel b) surrounding titanium implant; (panel c) surrounding nanotubular implant; results indicate no fibrous scar tissue formation for both titanium and nanotubular implant and the tissues are very similar to the control tissue, dotted line shows where the implant was in contact with tissues.

It is crucial that any new biomaterial used for orthopedic applications must demonstrate appropriate biocompatibility. Thus the in vivo biocompatibility of titanium and nanotubular surfaces was investigated by implanting discs of titanium and nanotubular titania subcutaneously. After 4 weeks, the implants were retrieved and biocompatibility was evaluated by histological analysis of the tissue surrounding the implant. FIG. 7 shows a light microscopy image of sections of healthy tissue and the tissue surrounding the implant stained with haematoxylin and eosin. FIG. 7, panel a, shows histology sections of healthy tissue. There is no fibrous scar tissue present in the tissues surrounding the titanium implant and comparable to healthy tissue (FIG. 7, panel b). Titanium is known to be biocompatible, and therefore should not cause any undesirable immune response in vivo. FIG. 7, panel c, shows light microscopy images of tissue sections surrounding the nanotubular titania implant. Similar to titanium, there is no fibrous scar tissue formation around the implant. The tissue appears to be healthy and normal. Thus, these preliminary in vivo results show that the nanotubular surfaces do not cause any adverse immune response under in vivo conditions.

The development of nanostructured platforms based on novel metal-oxide films can provide insight into cell-material interactions for the development of improved implant surfaces. The results provided herein show that nanotubular titania surfaces provide a favorable template for bone cell growth and differentiation. Nanotubular titania surfaces were fabricated by a simple anodization process and were used to investigate short term and long term performance of MSCs. The results show that these surfaces supported higher cell adhesion, proliferation and viability up to 7 days of culture when compared to titanium surfaces. Cells cultured on nanotubular surfaces demonstrated higher ALP activity. Furthermore, the calcium and phosphorous concentrations were 50% higher on these surfaces showing that matrix deposition was upregulated on nanotubular surfaces. Moreover, the nanotubular surfaces do not cause adverse immune response under in vivo conditions. Thus, the results show that osteoblast activity can be significantly enhanced using controlled nanotopographies. Therefore, incorporation of such nanoarchitectures on implant surfaces will further facilitate the culture and maintenance of differentiated cell states, and promote long-term osseointegration Example 2

Fabrication of Drug Eluting Nanotubular Surface Coated Implants

It was next determined whether the nanotubes may be filled with antibiotics that would ward off infection immediately after implantation (e.g., gentamicin, chlorhexidine diacetate, ciprofloxacin) or with growth factors or therapeutic proteins (e.g., TGF-β, IGF, BMP) that will help to stimulate cellular differentiation and bone repair processes. In this study, bovine serum albumin (BSA) and lysozyme (LYS) were used as model proteins to investigate their loading and release efficiencies from nanotube architectures. BSA is a larger molecule with a net negative charge at neutral pH compared to LYS which is smaller in size with a net positive charge at neutral pH (Table 2).

TABLE 2

|  | Molecular Weight (KDa) | Isoelectric Point pI | Net charge @ pH 7.0 |
| --- | --- | --- | --- |
| Bovine Serum Albumin | 67 | 4.7 | −18 |
| Lysozyme | 14 | 11 | +7 |

Figure 8:
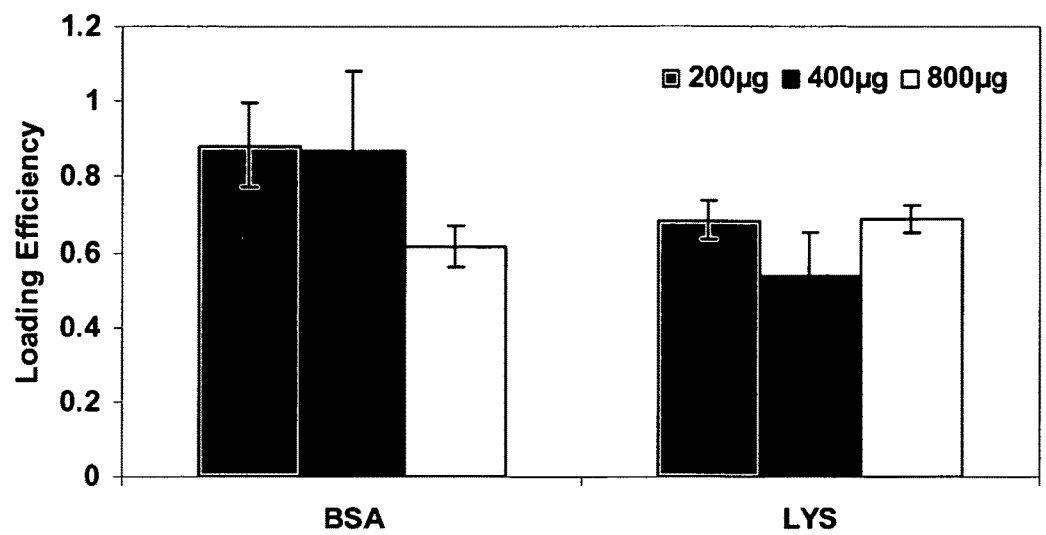
FIG. 8 is graph showing the loading efficiencies of bovine serum albumin (BSA) and lysozyme (LYS) in nanotubes.

Before the release studies were performed, it was important to evaluate the loading efficiency of the proteins on the nanotube surface. The concentrations of the original and the rinse solutions were measured using a commercially available Micro-BCA assay kit. The loading efficiency was expressed as percentage of loaded protein after washing. The loading efficiency was calculated by the following equation:

$$\eta = \frac{C_o - C_r}{C_o} \quad (1)$$

where η: loading efficiency
$C_o$: protein concentration in the original solution
$C_r$: protein concentration in the rinse solution FIG. 8 shows loading efficiencies for nanotubes loaded with 200, 400 and 800 µg of both BSA and LYS. The results show that approximately 60-80% of protein is retained in the nanotubes after washing regardless of initial loading.

To evaluate the differences in amounts of protein in nanotubes, X-ray photoelectron spectroscopy (XPS) analysis was carried out. Table 3 shows the N/C ratios computed from XPS survey scans. LYS and BSA adsorbed surfaces were used as controls. There is a steady increase in N/C ratios with increasing amounts of protein loaded into the nanotubes. A more precise way to characterize protein on the surface is to determine the fraction of C—N and N—C═O peaks in overall C1s peak. The C—N and N—C═O peaks are characteristic of proteins which are at a shift of 0.8 eV and 1.8 eV respectively from the C—C peak (285 eV). Thus, high resolution C1s scans were taken and the peak fit analysis software provided with the XPS instrument was used to determine % of C—N and N—C═O in the overall C1s peak (Table 3). A convolution of Gaussian components was assumed for all the peaks. There is an increase in the intensity for the C—C, C—N and N—C═O peaks with increasing amounts of proteins loaded into the nanotubes. However, the survey and high resolution C1s scans for surfaces adsorbed with BSA and LYS show significantly lower protein concentrations on the surface. These results show that the nanotubes can be successfully loaded with measured amounts of proteins using the technique described here.

TABLE 3

|  | Bovine Serum Albumin | | | | Lysozyme | | | |
| --- | --- | --- | --- | --- | --- | --- | --- | --- |
|  | Adsorbed | 200 mg | 400 mg | 800 mg | Adsorbed | 200 mg | 400 mg | 800 mg |
| N/C | 0.123 | 0.188 | 0.233 | 0.268 | 0.215 | 0.245 | 0.268 | 0.297 |
| C—C | 0.81 | 0.71 | 0.51 | 0.40 | 0.73 | 0.53 | 0.32 | 0.21 |
| C—N | 0.11 | 0.18 | 0.24 | 0.20 | 0.22 | 0.29 | 0.35 | 0.40 |
| N—C═O | 0.08 | 0.11 | 0.25 | 0.40 | 0.03 | 0.18 | 0.31 | 0.39 |

Figure 9:
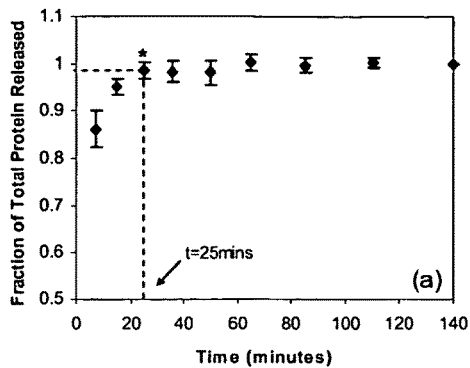
FIG. 9 is a series of graphs showing the fraction of total protein released from nanotubes filled with 200 mg (Panel A), 400 mg (Panel B) and 800 mg (Panel C) of BSA and 200 mg (Panel D), 400 mg (Panel E) and 800 mg (Panel F) of LYS. The time point at which all the protein is released is indicated by dotted line. Concentrations at these time points are significant different then those for time points before, however not significantly different then the time points after, $p<0.05$, $n=3$
Figure 9:
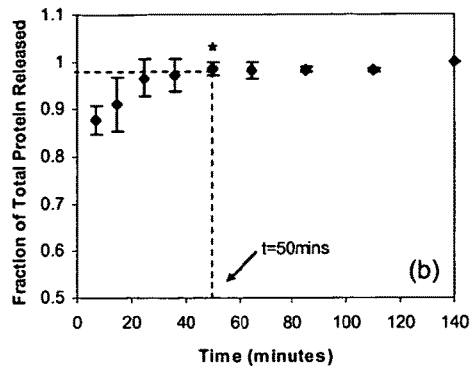
Figure 9:
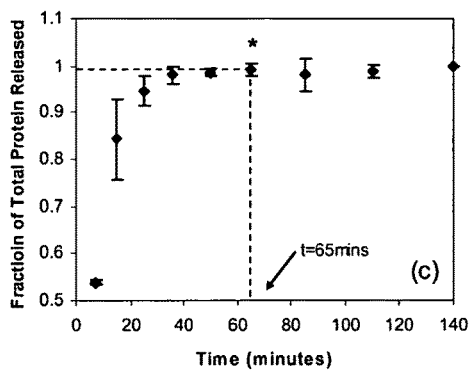
Figure 9:
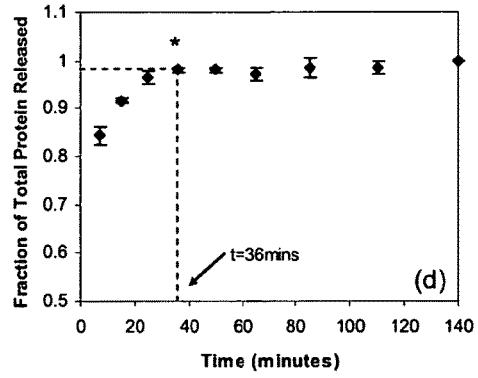
Figure 9:
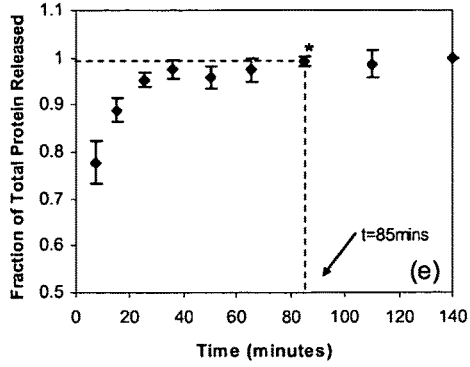
Figure 9:
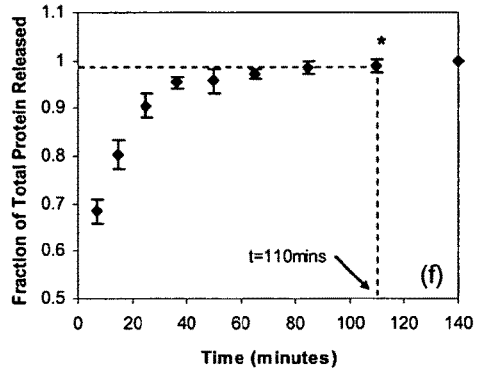

FIG. 9 shows the release data obtained from nanotubes loaded with 200, 400 and 800 µg of BSA and LYS. The amount of protein eluted is expressed in terms of fraction of total protein released. The results show that two different proteins, a larger negative molecule (BSA, FIG. 9, Panels A, B and C) and a smaller positive molecule (LYS; FIG. 9, Panels D, E and F), can be easily released from the nanotubes. Further, the release kinetics can be altered by changing the amount of protein loaded. Table 4 shows the time points at which all the protein is released from the nanotubes.

As expected, there is slower and sustained release from the nanotubes loaded with a higher amount of protein compared to those loaded with lower amounts of protein. Also, the data shows that LYS release from the nanotubes is much slower compared to that of BSA. It is thought that this is due to the difference between the negatively and positively charged proteins interacting with surface charge of the nanotube interface. The surfaces of most metal oxide films are inherently charged as a consequence of the equilibration of charged crystalline lattice defects within the surface. Depending on the net concentration of lattice defects the surface may be positively or negative charged. The surface of titania nanotubes consists of terminal hydroxyl groups which results in mild negative charge on the surface. Thus, the fact that the release of LYS which is positively charged is much slower compared to that of BSA which is negatively charged may be due to a stronger electrostatic interaction between the LYS and the titania surface.

TABLE 4

|  | Bovine Serum Albumin | Lysozyme |
| --- | --- | --- |
| 200 µg | 25 | 36 |
| 400 µg | 50 | 85 |
| 800 µg | 65 | 110 |

This study shows that titania nanotubes can be easily fabricated with an anodization process and. These nanotubes can also be optionally loaded with drugs or biological agents such as proteins. Moreover, the release or elution of the drugs or biological agents from the nanotubes can be controlled by varying the tube length, diameter and wall thickness. Here, we have shown that the release rates of BSA and LYS can be controlled by varying their loading into the nanotubes themselves the amounts loaded into nanotubes. Furthermore, by changing the nanotube diameter, wall thickness and length, the release kinetics can be altered for specific drugs in order to achieve sustained release of the drug over a period of time. Thus, these nanotubular surfaces have potential applications in orthopedics, specifically for implants where faster osseointegration is desired along with controlled release of drugs such as antibiotics or growth factors.

What is claimed is:

1. A composition, comprising:
a surface or film comprising a vertically oriented array of a plurality of nanotubes or microwells, where a bioactive agent is filled into the nanotubes or microwells themselves and wherein a first end of the array of the plurality of filled nanotubes or microwells is in contact with the surface or film, and wherein the plurality of nanotubes or microwells is capped with a polymeric erodible capping film to provide for delayed elution of the bioactive agent from within the nanotubes or microwells to the surrounding tissue upon placement in a subject and erosion of the capping film.

2. The composition of claim 1, wherein said composition is an orthopedic implant, a dental implant, a cardiovascular implant, a neurological implant, a neurovascular implant, a gastrointestinal implant, a muscular implant, or an ocular implant.

3. The composition of claim 1, wherein said composition is a patch for localized delivery of said bioactive agent to a soft tissue.

4. The composition of claim 1, wherein said surface or film unfurls in the presence of a hydrating liquid.

5. The composition of claim 1, wherein said surface or film further comprises a covalently attached bioactive agent.

6. The composition of claim 1, wherein said surface or film is comprised of poly(DL-lactide-co-glycolide) (PLGA), poly(DL-lactide-co-ε-caprolactone) (DLPLCL), poly(ε-caprolactone) (PCL), gelatin, agarose, poly(methyl methacrylate),galatin/ε-caprolactone, collagen-GAG, collagen, fibrin, PLA, PGA, PLA-PGA co-polymers, poly(anhydrides), poly(hydroxy acids), poly(ortho esters), poly(propylfumerates), poly(caprolactones), poly(hydroxyvalerate), polyamides, polyamino acids, polyacetals, biodegradable polycyanoacrylates, biodegradable polyurethanes and polysaccharides, polypyrrole, polyanilines, polythiophene, polystyrene, polyesters, non-biodegradable polyurethanes, polyureas, poly(ethylene vinyl acetate), polypropylene, polymethacrylate, polyethylene, polycarbonates, poly(ethylene oxide), co-polymers of the above, mixtures of the above, and adducts of the above, or combinations thereof.

7. The composition of claim 1, wherein said surface or film is comprised of silicon, titania, zirconia, cobalt-chromium, alumina, silica, barium aluminate, barium titanate, iron oxide, and zinc oxide, nitinol, elastinite, tantalum, elgiloy, phynox, Ti6A14V, CoCr, TiC, TiN, L605, 316, MP35N, MP20N, stainless steel alloy, 316L stainless steel alloy, 304 stainless steel alloy, or combinations thereof.

8. The composition of claim 1, wherein said nanotubes or microwells further comprise an agent to facilitate cell adhesion and cell growth selected from the group consisting of laminin, fibrin, fibronectin, proteoglycans, glycoproteins, glycosaminoglycans, chemotactic agents, and growth factors.

9. The composition of claim 1, wherein said bioactive agent is selected from a polypeptide, growth factor, a steroid agent, an antibody therapy, an antibody fragment, a DNA, an RNA, and siRNA, an antimicrobial agent, an antibiotic, an antiretroviral drug, an anti-inflammatory compound, an antitumor agent, anti-angiogeneic agent, and a chemotherapeutic agent.

10. The composition of claim 1, wherein said nanotubes range in length from about 1 μm to about 500 μm.

11. The composition of claim 1, wherein said nanotubes range in length from about 1 μm to about 70 μm.

12. The composition of claim 1, wherein said nanotubes range in diameter from about 3 nm to about 300 nm.

13. The composition of claim 12, wherein said surface or film comprises nanotubes at a density greater than 10,000,000 nanotubes per square centimeter.

14. The composition of claim 12, wherein said surface or film comprises nanotubes at a density greater than 25,000,000 nanotubes per square centimeter, wherein said density provides for an extracellular matrix compatible tissue adhesive.

15. The composition of claim 1, wherein said nanotubes have a pore diameter range from about 3 nm to about 250 nm.

16. The composition of claim 1, wherein said surface or film ranges in thickness from about 1 μm to about 2.5 mm.

17. The composition of claim 1, wherein said surface or film ranges in thickness from about 1 μm to about 750 μm.

18. The composition of claim 1, wherein said surface or film ranges in thickness from about 1 μm to about 200 μm.

19. The composition of claim 1, wherein said surface or film ranges in thickness from about 1 μm to about 150 μm.

20. The composition of claim 1, wherein said microwells range in diameter from about 1 μm to about 150 μm.

21. The composition of claim 20, wherein said surface or film comprises microwells at a density greater than 150,000 microwells per square centimeter.

22. The composition of claim 1, wherein said surface or film further comprises cells.

23. The composition of claim 22, wherein said cell is a stem cell, a retinal progenitor cell, a cardiac progenitor cell, an osteoprogenitor cell, or a neuronal progenitor cell.

* * * * *

UNITED STATES PATENT AND TRADEMARK OFFICE
CERTIFICATE OF CORRECTION

PATENT NO. : 9,775,932 B2
APPLICATION NO. : 12/530015
DATED : October 3, 2017
INVENTOR(S) : Tejal Ashwin Desai et al.

It is certified that error appears in the above-identified patent and that said Letters Patent is hereby corrected as shown below:

On the Title Page

Item [75], delete "Ketal C. Popat" and insert --Ketul C. Popat--.

Signed and Sealed this
Fifth Day of February, 2019

Andrei Iancu
*Director of the United States Patent and Trademark Office*